United States Patent [19]

Sano et al.

[11] 4,229,373

[45] Oct. 21, 1980

[54] PROCESS FOR PRODUCING DIMETHYL FORMAMIDE

[75] Inventors: Kozo Sano; Hidetaka Kiga; Takeo Ikarashi, all of Niigata, Japan

[73] Assignee: Mitsubishi Gas Chemical Company, Inc., Tokyo, Japan

[21] Appl. No.: 41,627

[22] Filed: May 23, 1979

[30] Foreign Application Priority Data

Jun. 1, 1978 [JP] Japan ................................ 53-66151

[51] Int. Cl.$^3$ .................. C07C 102/00; C07C 103/36
[52] U.S. Cl. ............................................... 260/561 R
[58] Field of Search ................................... 260/561 R

[56] References Cited

U.S. PATENT DOCUMENTS

| | | | |
|---|---|---|---|
| 2,677,706 | 5/1954 | Giachino | 260/561 R |
| 3,446,842 | 5/1969 | Nozaki | 260/561 R |
| 4,094,905 | 6/1978 | Mizuno et al. | 260/561 R |

FOREIGN PATENT DOCUMENTS 31-6510  4/1956  Japan.
718759  11/1954  United Kingdom.

*Primary Examiner*—Arthur P. Demers
*Attorney, Agent, or Firm*—Armstrong, Nikaido, Marmelstein & Kubovcik

[57] ABSTRACT

Dimethyl formamide is produced in a considerably high yield by reaction of monomethylamine and triethylamine, or monomethylamine, trimethylamine and dimethylamine with carbon monoxide in the presence of metallic iron or an iron compound as a catalyst, while adding 2–20 moles of free water per gram-atom of iron of the catalyst to the reaction system.

16 Claims, No Drawings

PROCESS FOR PRODUCING DIMETHYL FORMAMIDE

This invention relates to a process for producing dimethyl formamide by reaction of (a) monomethylamine and trimethylamine or (b) monomethylamine, trimethylamine and dimethylamine with carbon monoxide in the presence of metallic iron or an iron compound as a catalyst, characterized by adding free water to the reaction system.

Generally, dimethyl formamide is produced by reaction of dimethylamine with carbon monoxide or methyl formate. The dimethylamine used as the starting material in the process is usually prepared by dehydration reaction of methyl alcohol and ammonia, but it is difficult to selectively produce only the dimethylamine, and a large amount of monomethylamine and trimethylamine are inevitably produced in addition to the dimethylamine. However, an industrial demand for monomethylamine and trimethylamine are smaller than that for dimethylamine, and thus most of these two kinds of amines are usually recycled to a methylamine synthesis system, where they are converted to dimethylamine. That is, synthesis of dimethyl formamide directly from mixed methylamines containing monomethylamine and trimethylamine having a smaller demand in place of pure dimethylamine will have a great industrial significance, because a considerable rationalization can be brought into the methylamine industry.

U.S. Pat. No. 2,677,706 discloses a process based on a reaction of monomethylamine and/or dimethylamine or a further mixture with trimethylamine with carbon monoxide in the presence of cuprous chloride, cupric chloride, potassium acetate, boron trifluoride or ammonium chloride as a catalyst as such an attempt. However, the selectivity of monomethylamine and trimethylamine to dimethyl formamide is low in said process, and thus the process is not industrially satisfactory.

U.S. Pat. No. 3,446,842 discloses a process for synthesizing dimethyl formamide from trimethylamine, ammonia and carbon monoxide, using dicobalt octacarbonyl as a catalyst, but the process has such disadvantages as a long reaction time, etc., and is not always industrially satisfactory.

The present inventors invented a process for producing dimethyl formamide from monomethylamine and trimethylamine or monomethylamine, trimethylamine and dimethylamine as starting materials, using metallic iron or an iron compound to overcome the disadvantages of the prior art (U.S. Patent application Ser. No. 917,894; British Patent Application No. 27465/78; DOS 2827633). As a result of further studies, inventors have found that the yield of dimethyl formamide can be considerably increased by adding free water to the reaction system of said process, and have established a new process.

The catalyst used in the present invention is metallic iron or iron compounds, and the iron compounds include oxides, halides, and hydroxides of iron or inorganic acid salts of iron such as sulfates, carbonates, etc., organic acid salts of iron such as formates, oxalates, acetates, etc., and carbonyl compounds of iron, such as iron pentacarbonyl, etc.

The amount of free water to be added to the reaction system is 2-20 moles, preferably 5-15 mols per gram-atom of iron of the metallic iron or the iron compound used as the catalyst. When free water is added thereto in excess of 20 moles, the yield of dimethyl formamide is low. Thus, the excess amount of free water is not preferable.

The amount of the catalyst to be used is 0.01-300 milligram-atom, preferably 0.1-300 milligram-atom, more preferably 1-100 milligram-atom, of iron in terms of iron atom per mole of amines as the starting materials. When the amount of the catalyst is less than the lower limit of said range, the yield is low, whereas the amount of the catalyst exceeding said upper limit of the range is not objectionable, but economically not advantageous.

In the present invention, use of the so-called solvent is not essential, but addition of a small amount of a solvent can provide a liquid phase portion even at the initial stage of reaction at a temperature above the critical temperature of the amines as the starting materials, and thus can facilitate temperature control and improve the yield. The following solvents are applicable to the present invention: amides such as dimethyl formamide, N-methylpyrolidone, etc., saturated aliphatic hydrocarbons such as hexane, heptane, octane, etc., and aromatic hydrocarbons such as benzene, toluene, xylene, etc.

A molar ratio of trimethylamine to monomethylamine to be used in the present invention is 0.1-10, preferably 0.5-5. The ratio outside said range is not practical, because of an increase in the amount of unreacted materials, or monomethyl formamide formed. On the other hand, a molar ratio of dimethylamine to monomethylamine and trimethylamine is not particularly limited, and can be selected freely in any molar ratio.

Reaction can be carried out under a pressure of at least 10 kg/cm² gage, preferably 50-500 kg/cm² gage. A lower pressure than the lower limit of said range is not preferable, because side reactions are promoted, whereas a higher pressure is not objectionable from the standpoint of reaction, but too high a pressure is not practical in view of process economy.

Carbon monoxide plays a role of raw material as well as a role of maintaining the reaction pressure. Thus, carbon monoxide is used in great excess, but can be used in a mixture with an inert gas such as nitrogen, etc., so far as the partial pressure of carbon monoxide is at least 10 kg/cm² gage.

Reaction can be carried out at a temperature of 50°–350° C., preferably 100°–300° C. A satisfactory reaction rate cannot be obtained at a temperature lower than 50° C., whereas the product is liable to be decomposed, resulting in reduction in yield, etc. at a temperature higher than 350° C. Thus, the temperature outside said range should not be used.

Reaction can be carried out batch-wise or continuously.

It has not been clarified yet what type of reaction occurs in the process of forming dimethyl formamide from the amines as the starting materials, but it seems, in view of relations between the starting materials and the product, that, when monomethylamine and trimethylamine are used as the starting materials, reaction represented by the following formula (1) takes place, and, when monomethylamine, dimethylamine and trimethylamine are used as the starting materials, reaction represented by the following formula (1) and reaction represented by the following formula (2) take place at the same time.

$$CH_3NH_2 + (CH_3)_3N + 2CO \rightarrow 2HCON(CH_3)_2 \qquad (1)$$

$$(CH_3)_2NH + CO \rightarrow 2HCON(CH_3)_2 \quad (2)$$

Mechanism of how the added water to the reaction system gives an effect upon these reactions has not been clarified yet.

According to the present invention, dimethyl formamide can be produced in a very high yield, using monomethylamine and trimethylamine having a smaller demand among the methylamines as the whole or a portion of the starting materials, and thus the present invention has a very great industrial significance.

The present invention will be described below in detail, referring to Examples and Comparative Examples. Throughout Examples and Comparative Examples, dimethyl formamide yield is based on total amines used as the starting materials.

EXAMPLE 1

229.6 m moles of monomethylamine, 166.0 m moles of trimethylamine, 5.77 m moles of anhydrous ferrous sulfate as a catalyst, and 56.3 m moles of water were charged into an autoclave having a net capacity of 100 ml, and subjected to reaction at a temperature of 210° C. under a pressure of 200 kg/cm² gage attained by carbon monoxide for 2 hours. The resulting product was analyzed by gas chromatography, and it was found that dimethyl formamide was obtained in a yield of 47.3%.

COMPARATIVE EXAMPLE 1

223.4 m moles of monomethylamine, 163.1 m mole of trimethylamine, and 6.45 m moles of anhydrous ferrous sulfate as a catalyst were used. Reaction was carried out in the same manner as in Example 1, except that the temperature was 203° C., and as a result dimethyl formamide was obtained in a yield of 31.4%.

EXAMPLES 2–11 AND COMPARATIVE EXAMPLES 2–5

Reaction was carried out by changing combinations of starting materials, catalyst, amount of water added, and other conditions variously, and the results are shown in the following Table together with those of Example 1, and Comparative Example 1.

TABLE

|  | Ex. 1 | Ex. 2 | Ex. 3 | Ex. 4 | Ex. 5 | Ex. 6 |
|---|---|---|---|---|---|---|
| Catalyst | FeSO$_4$ | FeSO$_4$ | FeSO$_4$ | FeSO$_4$ | Fe(CO)$_5$ | FeSO$_4$ |
| Amount of catalyst as Fe atom (mg atom) | 5.77 | 6.34 | 5.77 | 5.77 | 6.43 | 6.39 |
| Amount of water added (m mol) | 56.3 | 45.6 | 24.2 | 105.1 | 51.1 | 44.4 |
| Ratio of water added to catalyst (mol/g atom) | 9.8 | 7.2 | 4.2 | 18.2 | 8.1 | 6.9 |
| Amount of monomethylamine (m mol) | 229.6 | 244.7 | 225.7 | 228.0 | 224.1 | 115.0 |
| Amount of trimethylamine (m mol) | 166.0 | 169.5 | 161.7 | 163.3 | 161.2 | 98.8 |
| Amount of dimethylamine (m mol) | 0 | 0 | 0 | 0 | 0 | 120.5 |
| Reaction temp. (°C.) | 210 | 205 | 205 | 205 | 207 | 203 |
| Reaction Pressure (kg/cm² gage) | 200 | 200 | 200 | 200 | 200 | 190 |
| Reaction time (hr.) | 2 | 2 | 2 | 2 | 2 | 2 |
| Production (m mol) |  |  |  |  |  |  |
| Dimethyl formamide | 187.3 | 174.0 | 154.6 | 145.6 | 180.0 | 186.2 |
| Monomethyl formamide | 95.3 | 81.3 | 88.4 | 84.7 | 80.4 | 45.2 |
| Yield |  |  |  |  |  |  |
| Dimethyl formamide | 47.3 | 42.0 | 39.8 | 37.2 | 46.7 | 55.7 |
| Solvent: N-methylpyrolidone (6.0 g) | used | used | used | used | used | used |

| Ex. 7 | Ex. 8 | Ex. 9 | Ex. 10 | Ex. 11 | Comp. Ex. 1 | Comp. Ex. 2 | Comp. Ex. 3 | Comp. Ex. 4 | Comp. Ex. 5 |
|---|---|---|---|---|---|---|---|---|---|
| Fe$_2$O$_3$ | FeCl$_2$ | Fe(CO)$_5$ | Fe(HCOO)$_3$ | Fe(OH)$_3$ | FeSO$_4$ | Fe(CO)$_5$ | FeSO$_4$ | Fe$_2$O$_3$ | FeCl$_2$ |
| 6.4 | 6.50 | 6.13 | 6.61 | 6.23 | 6.45 | 6.99 | 6.37 | 6.4 | 6.5 |
| 50.0 | 42.0 | 47.8 | 50.2 | 42.4 | 0 | 0 | 0 | 0 | 0 |
| 7.8 | 6.5 | 7.8 | 7.6 | 6.8 | 0 | 0 | 0 | 0 | 0 |
| 227.0 | 226.4 | 226.0 | 230.5 | 221.9 | 223.4 | 207.3 | 116.5 | 225.5 | 226.2 |
| 161.5 | 180.3 | 161.3 | 163.8 | 172.5 | 163.1 | 174.9 | 102.0 | 160.0 | 162.7 |
| 0 | 0 | 0 | 0 | 0 | 0 | 0 | 98.4 | 0 | 0 |
| 205 | 205 | 205 | 206 | 205 | 203 | 208 | 205 | 205 | 205 |
| 200 | 200 | 200 | 200 | 200 | 200 | 200 | 180 | 200 | 200 |
| 2 | 2 | 2 | 2 | 2 | 2 | 2 | 2 | 2 | 2 |
| 170.5 | 178.1 | 172.0 | 168.4 | 162.9 | 121.3 | 120.0 | 119.2 | 110.4 | 124.4 |
| 82.0 | 71.2 | 78.8 | 72.5 | 84.3 | 80.0 | 74.4 | 47.7 | 75.3 | 73.6 |
| 43.9 | 43.8 | 44.4 | 42.7 | 41.3 | 31.4 | 31.4 | 37.6 | 28.6 | 32.0 |
| used | used | not used | used | used | used | used | used | used | used |

What is claimed is:

1. In a process for producing dimethyl formamide by reacting: (a) monomethylamine and trimethylamine, or (b) monomethylamine, trimethylamine and dimethylamine with carbon monoxide in the presence of metallic iron or an iron compound as a catalyst, the improvement comprising adding free water to the reaction system.

2. A process according to claim 1, wherein 2–20 moles of free water is added to the reaction system per gram-atom of iron of the metallic iron or the iron compound as the catalyst.

3. A process according to claim 1, wherein 5–15 moles of free water is added to the reaction system per gram-atom of iron of the metallic iron or the iron compound as the catalyst.

4. A process according to claim 1, wherein a solvent is added to the reaction system.

5. A process according to claim 4, wherein the solvent is dimethyl formamide, N-methylpyrolidone, hexane, heptane, ocatne, benzene, toluene or xylene.

6. A process according to claim 1, wherein the iron compound is selected from oxides, halides, hydroxides, inorganic acid salts, organic acid salts and carbonyl compounds of iron.

7. A process according to claim 1, wherein the catalyst is used in an amount of 0.01–300 milligram-atoms as iron atom per mole of the amines as the starting materials.

8. A process according to claim 1, wherein the catalyst is used in an amount of 0.1–300 milligram-atoms as iron atom per mole of the amines as the starting materials.

9. A process according to claim 1, wherein the catalyst is used in an amount of 1–100 milligram-atom as iron atom per mole of the amines as the starting materials.

10. A process according to claim 1, wherein the monomethylamine and the trimethylamine are used at a molar ratio of trimethylamine to monomethylamine of 0.1–10.

11. A process according to claim 1, wherein the monomethylamine and the trimethylamine are used at a molar ratio of trimethylamine to monomethylamine of 0.5–5.

12. A process according to claim 1, wherein the reaction pressure is at least 10 kg/cm$^2$ gage.

13. A process according to claim 12, wherein the reaction pressure is 50–500 kg/cm$^2$ gage.

14. A process according to claim 1, wherein an inert gas is used where a partial pressure of the carbon monoxide is at least 10 kg/cm$^2$ gage.

15. A process according to claim 1, wherein reaction temperature is 50°–350° C.

16. A process according to claim 1, wherein reaction temperature is 100°–300° C.

* * * * *